(12) United States Patent
Munro et al.

(10) Patent No.: US 8,289,618 B2
(45) Date of Patent: Oct. 16, 2012

(54) RADIATION DIFFRACTION MATERIAL FOR REFLECTING INVISIBLE RADIATION

(75) Inventors: Calum H. Munro, Wexford, PA (US); Mark D. Merritt, State College, PA (US)

(73) Assignee: PPG Industries Ohio, Inc, Cleveland, OH (US)

( * ) Notice: Subject to any disclaimer, the term of this patent is extended or adjusted under 35 U.S.C. 154(b) by 0 days.

(21) Appl. No.: 12/879,322

(22) Filed: Sep. 10, 2010

(65) Prior Publication Data

US 2010/0328764 A1 Dec. 30, 2010

Related U.S. Application Data

(63) Continuation of application No. 11/263,679, filed on Nov. 1, 2005.

(51) Int. Cl.
*G02B 5/08* (2006.01)
*C08K 9/10* (2006.01)

(52) U.S. Cl. ......... 359/359; 427/162; 523/200; 523/201

(58) Field of Classification Search .................. 523/200, 523/201; 359/359
See application file for complete search history.

(56) References Cited

U.S. PATENT DOCUMENTS

| | | | |
|---|---|---|---|
| 5,122,905 A | 6/1992 | Wheatley et al. | |
| 5,281,370 A | 1/1994 | Asher et al. | |
| 5,527,386 A | 6/1996 | Statz | |
| 5,624,731 A | 4/1997 | Desjardins | |
| 5,711,884 A | 1/1998 | Asher et al. | |
| 5,783,120 A | 7/1998 | Ouderkirk et al. | |
| 5,824,733 A | 10/1998 | Dobert et al. | |
| 5,854,078 A | 12/1998 | Asher et al. | |
| 5,932,309 A | 8/1999 | Smith et al. | |
| 6,037,392 A | 3/2000 | Tang et al. | |
| 6,299,979 B1 | 10/2001 | Neubauer et al. | |
| 6,337,131 B1 | 1/2002 | Rupaner et al. | |
| 6,733,946 B2 * | 5/2004 | Kumacheva et al. | 430/138 |
| 6,894,086 B2 | 5/2005 | Munro et al. | |
| 2003/0125416 A1 | 7/2003 | Munro et al. | |
| 2005/0142343 A1 | 6/2005 | Winkler et al. | |
| 2005/0185686 A1 * | 8/2005 | Rupasov et al. | 372/43.01 |
| 2006/0191442 A1 | 8/2006 | He et al. | |
| 2006/0254315 A1 | 11/2006 | Winkler et al. | |
| 2007/0100026 A1 | 5/2007 | Munro et al. | |
| 2007/0165903 A1 | 7/2007 | Munro et al. | |

FOREIGN PATENT DOCUMENTS

DE 102 45 848 A1 4/2004

(Continued)

OTHER PUBLICATIONS

Kang et al., Micelle-Encapsulated Carbon Nanotubes: A Route to Nanotube Composites, J Am Chem Soc, 2003, pp. 5650-5651, vol. 125.

(Continued)

*Primary Examiner* — Vickey Nerangis
(74) *Attorney, Agent, or Firm* — Julie W. Meder

(57) ABSTRACT

A method of controlling radiation reflected from a surface comprising: applying a composite material to a surface, where the composite material comprises an ordered periodic array of particles held in a polymeric matrix material; exposing the surface bearing the composite material to radiation; and reflecting invisible radiation from the composite material on the surface.

14 Claims, 2 Drawing Sheets

FOREIGN PATENT DOCUMENTS

| | | | |
|---|---|---|---|
| EP | 0 955 323 | A1 | 11/1999 |
| RU | 2130041 | C1 | 5/1999 |
| RU | 2254351 | C2 | 6/2005 |
| WO | 9722667 | A1 | 6/1997 |
| WO | 2004/098793 | A2 | 11/2004 |

OTHER PUBLICATIONS

Pfaff et al.; "Angle-Dependent Optical Effects Deriving from Submicron Structures of Films and Pigments"; Chem. Rev.; 1999; 1963-1981; 99.

* cited by examiner

RADIATION DIFFRACTION MATERIAL FOR REFLECTING INVISIBLE RADIATION

CROSS-REFERENCE TO RELATED APPLICATIONS

This application is a continuation application of U.S. patent application Ser. No. 11/263,679, filed Nov. 1, 2005. The entire contents of the above-referenced application is incorporated herein by reference.

FIELD OF THE INVENTION

This invention relates to Bragg diffracting colorants produced from core-shell particles.

BACKGROUND OF THE INVENTION

Goniochromaticity is the effect of perceived color varying as the angle of illumination or observation varies. Goniochromatic pigments are used, for example, in automotive coatings, decorative coatings, plastic pigmentation, printing inks (security inks in particular), textiles and cosmetics. Their optical effect results from the directional reflection of light from predominantly sheet-like particles that conventionally are metallic or that have a structured refractive index contrast, the length scale of which is comparable to the wavelength of light. According to the nature of the pigment particles, the pigments are known as metallic effect pigments (for example, aluminum, zinc, copper or alloys thereof) or interference pigments (for example, based on titanium dioxide-coated mica, such as muscovite, phlogopite and biotite).

As a result of the incident light being reflected directionally by the predominantly sheet-like particles, color effect pigments that are oriented, for example, in a coating, exhibit goniochromaticity; that is, their perceived color (lightness and/or hue and/or chroma) varies with the angle of illumination or observation.

There is a need for durable goniochromatic materials that can be produced in particulate form and that are suitable for use as colorants with minimal haze.

SUMMARY OF THE INVENTION

The present invention is directed to a radiation diffraction material comprising an ordered periodic array of particles held in a polymeric matrix wherein said particles each comprise a core surrounded by a shell of a non-film forming composition that is different from said matrix.

The present invention is further directed to a method of producing a radiation diffractive material comprising the steps of: applying a dispersion of core-shell particles onto a substrate, the cores being substantially non-swellable and the shells being non-film forming; arranging the particles in an ordered periodic array that diffracts radiation; coating the array of particles with a matrix composition; swelling the shells by diffusing components of the matrix into the shells; and fixing the coated array of particles.

The present method is further directed to a system for producing radiation diffractive material comprising: a substrate for receiving a dispersion of core-shell particles that form an ordered periodic array, the shells being swellable and substantially non-film-forming; a matrix delivery device for coating the array with a matrix composition; a radiation source for illuminating the coated array; a radiation detector for measuring the spectrum of radiation diffracted by the coated array; and a curing system for curing components in the coated array and fixing the relative positions of the particles.

DETAILED DESCRIPTION OF THE INVENTION

The present invention provides radiation diffractive materials comprising an ordered periodic array of core-shell particles fixed within a matrix with the shell material being non-film forming and different from the matrix material. The materials are suitable for use in particulate form as colorants, among other things. As used herein, the term "colorants" refers to radiation diffractive materials that diffract radiation in the visible spectrum, while radiation diffractive material refers to material that diffracts any wavelength of electromagnetic radiation.

In certain embodiments, the core material and the shell material may have different indices of refraction. In addition, the refractive index of the shell may vary as a function of the shell thickness as a gradient of refractive index through the shell thickness. The refractive index gradient is a result of a gradient in the composition of the shell material through the shell thickness.

In one embodiment of the invention, the gradient through the shell thickness of composition and properties is produced by applying a dispersion of polymerizable core-shell particles onto a substrate, the cores being substantially non-swellable and the shells being non-film forming. The particles are arranged into an ordered periodic array that diffracts radiation, and the array of particles is coated with a matrix composition. One or more components of the matrix diffuse into the shells resulting in gradients of the shell composition and of the properties of the shell. The matrix composition may include crosslinkable monomers. Polymerization of the matrix monomers in the shell and in the matrix fixes the array.

The present invention includes a system for producing radiation diffractive material having a substrate for receiving a dispersion of particles that form an ordered periodic array and a matrix delivery device for coating the array with a matrix composition. A radiation source is arranged to illuminate the coated array while a radiation detector measures the spectrum of radiation diffracted by the coated array. The spacing between the particles is adjusted to achieve a desired wavelength of diffracted radiation. A curing system cures components in the coated array and fixes the relative positions of the particles.

Figure 1:
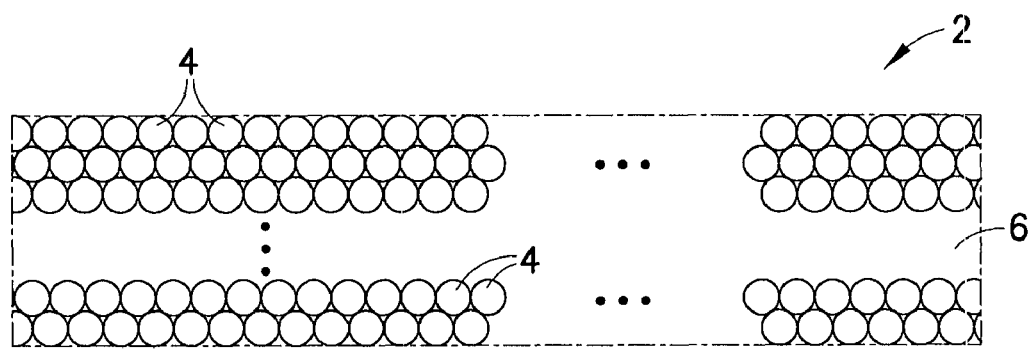
FIG. 1 is a cross-section of radiation diffractive material made in accordance with the present invention.
Figure 2:
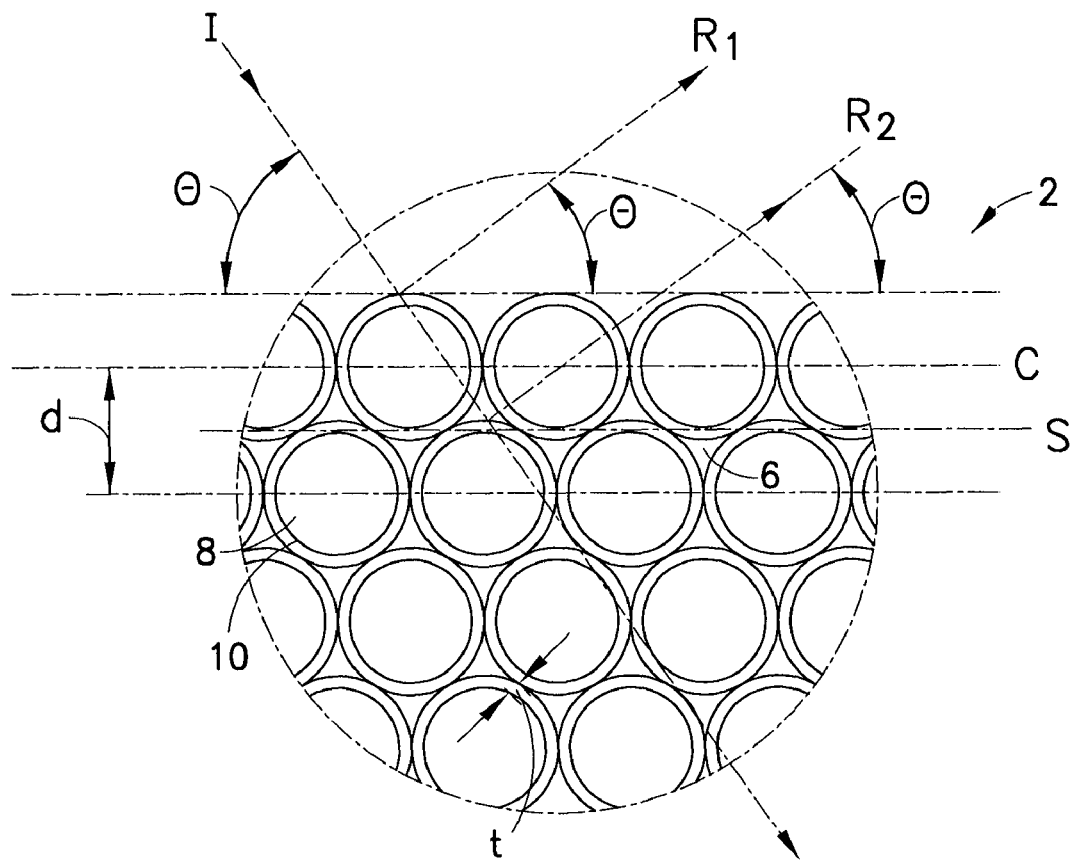
FIG. 2 is a detailed view of the radiation diffractive material of FIG. 1 showing Bragg diffraction of visible light at one viewing angle.

Referring to FIGS. 1 and 2, the radiation diffraction material 2 of the present invention includes an ordered periodic array of particles 4 held in a polymeric matrix 6. The particles 4 are composed of a core 8 surrounded by a shell 10. The material of the shell 10 is non-film forming and is different from the material of the matrix 6. As such, the array includes at least three general regions, namely, the matrix 6, the particle shell 10 and the particle core 8. Typically, the particles 4 are generally spherical with the diameter of the core 8 constituting 80 to 90 percent of the total particle diameter or 85 percent of the total particle diameter with the shell 10 constituting the balance of the particle diameter and having a radial thickness dimension. The core material and the shell material have different indices of refraction. In addition, the refractive index of the shell varies as a function of the shell thickness in the form of a gradient of refractive index through the shell thickness. The refractive index gradient is a result of a gradient in the composition of the shell material through the shell thickness.

The matrix material is an organic polymer such as a polystyrene, a polyurethane, an acrylic polymer, an alkyd polymer, a polyester, a siloxane-containing polymer, a polysulfide, an epoxy-containing polymer, or a polymer derived from an epoxy-containing polymer. The material of the particle cores is also polymeric and may be chosen from the same polymers as the matrix material and may also be inorganic material such as a metal oxide (e.g., alumina, silica or titanium dioxide) or a semiconductor (e.g., cadmium selenide). The polymer(s) of the particle shells may be selected from the same list of polymers as the matrix material; however, for a particular array of particles, the polymer(s) of the particle shell differ from the polymer(s) of the matrix material. By "non-film forming", it is meant that the shell material remains in position surrounding each particle core without forming a film of the shell material; as such, the core-shell particles are discrete particles within the matrix material. Such core-shell particles may be produced by emulsion polymerization of core monomers followed by polymerization of shell monomers thereover.

The resultant core-shell particles are arranged into an ordered array by dispersing the core-shell particles in a carrier and coating the dispersion onto a substrate. The dispersion of the particles may contain 1 to 70 vol. % of the particles, or 30 to 65 vol. % of the particles. A suitable composition for the carrier is water. The dispersion may be coated onto a substrate by various techniques including dipping, spraying, brushing, roll coating, gravure coating, curtain coating, flow coating, slot-die coating, or ink-jet coating. The particles in the dispersion are all similarly charged, which causes them to repel each other and form a periodic array of particles. The substrate coated with a layer of the dispersion is dried to remove the carrier from the dispersion so that the particles pack substantially adjacent to each other in three dimensions. The drying may be achieved using forced air, or by convective or radiative heating of the substrate and/or the dispersion.

A precursor matrix material (containing monomers) is applied to the packed particles on the substrate by any suitable technique such as spraying, brushing, roll coating, gravure coating, curtain coating, flow coating, slot-die coating, or ink-jet coating and interpenetrates the array with a fluid matrix composition. The monomers of the matrix composition flow around the core-shell particles and fill into the interstitial spaces between the particles in the packed array. Some of the matrix monomer(s) diffuse into the shells of the particles, thereby swelling the shells and increasing the shell thickness. The matrix monomers diffuse into the shells as a gradient through the thickness of the shells with the highest concentration of matrix monomers being at the outer edge of the shell and the lowest concentration of matrix monomers being adjacent the interface between the shell and the core.

The matrix composition is cured (such as by exposure to ultra-violet light) to polymerize the matrix material in the interstices of the array and the matrix material that diffused into the particle shells thereby fixing the dimension of the shells and the position of the particles within the matrix polymer. Other curing mechanisms may be used to fix the matrix composition within and around the particles. The matrix monomers diffused into the shells polymerize within the shells creating a gradient of matrix polymer in the shell with the highest concentration of matrix polymer being at the outer edge of the shell adjacent the matrix and the lowest concentration of matrix polymer being adjacent the interface between the shell and the core.

Referring to FIG. 2, the array of particles 2 diffract radiation according to Bragg's law. Incident radiation (ray I) is partially reflected (ray $R_1$) at the uppermost layer of particles in the array at an angle $\Theta$ to the plane of the first layer and is partially transmitted (ray T) to underlying layers of particles. Some absorption of incident radiation occurs as well. The portion of transmitted radiation is then itself partially reflected (ray $R_2$) at the second layer of particles in the array at the angle $\Theta$ (with some absorption) and partially transmitted to underlying layers of particles. This feature of partial reflection at the angle $\Theta$ and partial transmission to underlying layers of particles continues through the thickness of the array. The wavelength of the reflected radiation satisfies the equation:

$$m\lambda = 2nd \sin \Theta$$

where (m) is an integer, (n) is the effective refractive index of the array and (d) is the distance between the layers of particles. The effective refractive index (n) is closely approximated as a volume average of the refractive index of the materials of the particles. For generally spherical particles, the dimension (d) is the distance between the plane of the centers of particles in each layer and is proportional to the particle diameter. In such a case, the reflected wavelength $\lambda$ is also proportional to the particle diameter.

Figure 3:
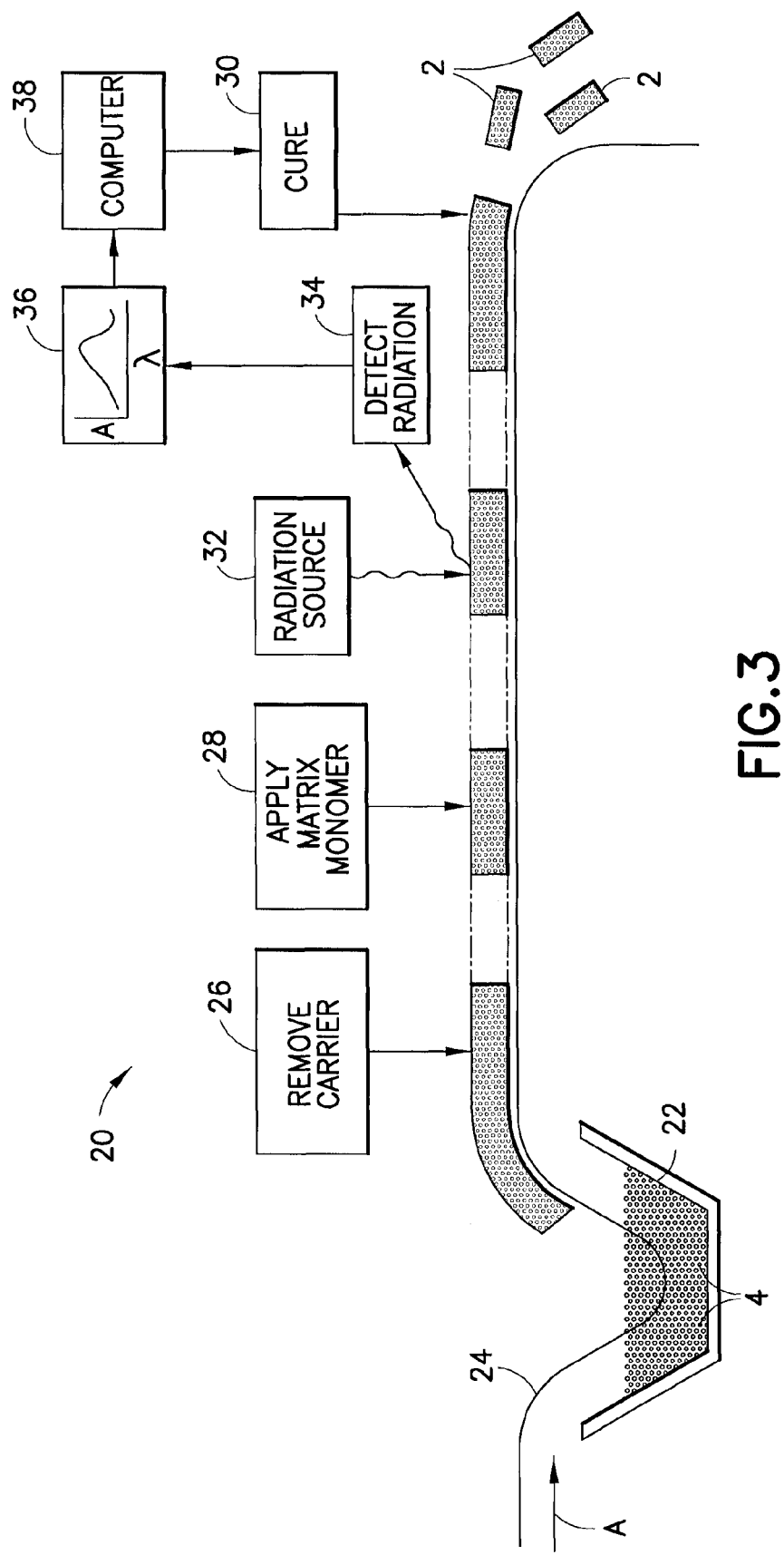
FIG. 3 is a schematic of a process for preparing the radiation diffractive material of the present invention.

The present invention further includes a system for producing radiation diffractive material. In one embodiment shown in FIG. 3, a dispersion 22 of particles 4 in a carrier is coated onto a substrate 24. FIG. 3 depicts the substrate 24 traveling in the direction of arrow A and being dipped into a vessel containing the dispersion 22 to coat the dispersion 22 onto the substrate 24, but this method of applying the dispersion 22 to the substrate 24 is not meant to be limiting and may include the methods described above. The particles 4 form into a periodic array and the carrier is removed from the dispersion at 26 (such as by evaporation) to yield essentially only a periodic array of particles 4 remaining on the substrate 24. The array of particles is interpenetrated with a fluid matrix monomer composition at 28. Some of the monomer composition diffuses into the shells, thereby increasing the shell thickness (and particle diameter) until the matrix composition is cured at 30. The length of time between application of the monomers onto the array and curing at 30 in part determines the degree of swelling by the shells.

The wavelength and intensity of the reflected light can be selected by varying the spacing (d) between the layers (by adjusting the size of the particles), the quantity of particle layers, the difference in the refractive index between the polymeric matrix and the particles, and the effective refractive index (n) of the radiation diffractive material according to Table 1.

TABLE 1

| Variable (with other variables constant) | Increased variable | Decreased variable |
| --- | --- | --- |
| Spacing between layers (d) | Longer $\lambda$ | Shorter $\lambda$ |
| Number of layers | Higher intensity | Lower intensity |
| Difference in refractive index between particles and matrix | Higher intensity | Lower intensity |

TABLE 1-continued

| Variable (with other variables constant) | Increased variable | Decreased variable |
|---|---|---|
| Degree of change in refractive index between matrix and particles Effective refractive index (n) | More scattering and haze Longer λ | Less scattering and haze Shorter λ |

The distance (d) between layers of particles in the array may be altered to shift the wavelength of diffracted radiation, i.e., increase the interparticle distance (d) to increase the wavelength or decrease the interparticle distance (d) to decrease the wavelength. It will be appreciated that the particle size of preformed particles having a fixed dimension is not readily adjusted in a continuous operation. Therefore, in one embodiment of the invention, when a change in particle size is necessary to adjust the diffraction wavelength, particles having a larger diameter may be used to prepare the array. This requires that the process be changed over to operation with different particles that may not allow for continuous preparation of array on the substrate. However, the core-shell particles of the present invention are particularly suited for on-line adjustment of particle size. The particle size is in part determined by the degree of swelling in the shell, i.e., the amount of matrix monomers that are allowed to diffuse into the shell prior to curing.

The periodic array of particles exhibits Bragg diffraction of radiation that may be monitored and controlled via an illuminating radiation source 32, a detector of diffracted radiation 34, including a spectrograph 36 (displaying absorbance as a function of wavelength) and a control system 38 for adjusting the wavelength of diffracted radiation. The illuminating radiation source 32 may include a light emitting diode (LED) and optical fibers for transporting illuminating light from the LED to the array and reflected light from the array back to the detector 34. The wavelength of illuminating radiation may be in the visible or non-visible spectrum. Radiation diffracted by the array and reflected back from the array is received by the detector and may be displayed on spectrograph 36. The system 20 includes a control system 38 (such as a computer with software) for correlating the measured spectrum of diffracted light with a desired appearance and for altering the wavelength of diffracted radiation. The control system 38 determines the length of time that the matrix monomers are allowed to diffuse into the particle shells. If the control system 38 determines that the wavelength of diffracted radiation is shorter than desired, the control system 38 increases the time before curing to allow more monomers to diffuse into the particle shells thereby increasing the particle diameter and increasing the interparticle distance (d). For example, the rate of travel of the substrate 24 may be slowed to increase the time for diffusion of matrix monomers into the particle shells before curing. A desired colored appearance of the array 2 can be selected using the computer 38 to correlate the reflected spectrum at 36 with apparent color. For example, a desired shade of blue light reflected from the array 2 has a signature spectrum of absorbance versus wavelength. When the computer 38 determines that the absorbance spectrum sufficiently matches the desired signature spectrum, the array 2 produced will exhibit the desired blue light. In this manner, production of the array 2 can be controlled based on the absorbance spectrum. It will be appreciated that other types of components for the radiation source 32, the detector 34, spectrograph 36 and control system 38 are within the scope of the invention.

The radiation diffractive material may remain on the substrate as a goniochromatic film covering the substrate. Alternatively, the radiation diffractive material may be removed from the substrate as a continuous film for application to a device such as by lamination using adhesives or the like. In another embodiment of the invention (as shown in FIG. 3), the radiation diffractive material is comminuted into particulate form (e.g., as flakes) for use as a colorant in a colored coating composition when the reflected radiation is visible light. The colored coating composition may be a paint, ink, a cosmetic or other decorative composition.

The average particle size of the particles is about 0.01 to about 1 micron or 0.06 to 0.5 micron. The distance (d) between the layers is controlled substantially by the size of the particles. If the particle size varies within a layer or if the particle size varies between layers, the spacing (d) between the layers will vary through the array. As noted above, the wavelength λ of light reflected under the Bragg condition is a function of the spacing (d) between the layers. A distribution in particle size causes variation in the wavelength of reflected light that is viewed as a broad bandwidth of light exhibiting a blend of colors instead of a clean, sharp color. Therefore, in order to maintain a regular array, the particles are similarly sized and, preferably, differ in size from each other by a maximum of 15% or a maximum of 5 percent.

For use in typical automotive coatings and industrial coatings (e.g., for cell phones) of conventional thickness, the radiation diffractive material may have a maximum thickness of 20 microns, such as 10 microns or less or 5 microns or less, such as 2 microns. Materials substantially thicker than 20 microns may be difficult to properly disperse and align in a typical automotive or industrial coating. Materials substantially thicker than 20 microns may also cause a roughening of the surface of a typical automotive or industrial coating, causing a reduction in the gloss of the coating, which may or may not be desirable. Thicker materials may be acceptable or desirable in other types of coatings that are thicker than automotive coatings, and may also be acceptable or desirable, for example, in plastic pigmentation, textiles and cosmetics and/or in applications wherein a "roughened" or reduced gloss appearance is desired. The number of layers of particles in the radiation diffractive material is selected to achieve the desired optical properties using the minimum number of layers for achieving the desired intensity of color. At these dimensions, the radiation diffractive material has an aspect ratio that allows materials in a coating composition to align with each other, and with the coated substrate, along their long axes. A suitable aspect ratio for the radiation diffractive material in an automotive coating composition is at least 2, or 5 to 100, such as 10.

The interference effect (the intensity of the reflected radiation) may be increased by increasing the number of layers in the array. While at least two layers are needed to induce a Bragg effect on the incident light, at least five or at least ten layers of particles can achieve a desired intensity of reflected radiation. Fewer layers of particles reflect less radiation thereby decreasing the intensity of the reflected radiation and tending to broaden the wavelength of the reflected radiation. More than about ten layers may be used in certain applications where higher intensity reflected radiation is desired. An increase in the shell thickness (i.e., increase in particle size) increases the distance (d) between layers of particles in the array, thereby increasing the wavelength of diffracted radiation.

The interference effect is also increased by increasing the difference in refractive index between the particles and the surrounding matrix. In conventional Bragg arrays of packed particles, the effective refractive index of the material in a plane through the centers of a layer of particles is close to the refractive index of the particles because little or no matrix material is found in that plane. A plane taken through the edges of the particles passes through matrix material and material of the particles. Hence, the effective refractive index through the plane of the particle edges is determined by both materials (matrix and conventional particle) and the difference in effective refractive index between the plane of the particle centers and a plane through the particle edges is somewhat less than the difference in refractive index between the particle material and the matrix material.

In contrast, the core-shell particles of the present invention provide greater difference in refractive index (and greater interference effect) than conventional particles due to the presence of the shell. The effective refractive index of the material 2 taken through a plane C through the centers of the particles is based primarily on the refractive index of the core material. The effective refractive index of the material 2 taken through a plane S through the shells of the particles is based on the refractive index of the shell material and the matrix material. In this manner, the difference in refractive index between the plane C and the plane S is maximized and can be greater than is achieved with conventional (not core-shell) particles.

In addition, while a greater difference in refractive index between the particles and the surrounding matrix induces greater intensity of reflected radiation, some scattering of incident radiation is typically associated with a step change in refractive index such as can exist between the matrix and particles of conventional Bragg arrays. Scattered incident radiation reduces the intensity of reflected radiation in the desired wavelength and broadens the spectrum of reflected radiation. For Bragg diffraction of light, the reflected color appears hazy. This undesired phenomenon of scattered radiation is minimized in the present invention where the change in refractive index of the radiation refractive material is less dramatic. The refractive index of the radiation refractive material shifts from the refractive index of the matrix polymer to a gradient of refractive index through the thickness of the shell corresponding to the gradient of concentration of matrix polymer through the shell thickness.

The present invention is not limited to use in diffracting visible light. Other wavelengths of electromagnetic radiation outside the visible spectrum may be reflected, such as ultraviolet radiation or infrared radiation. The ordered array in the matrix may be used to reflect such radiation to prevent or minimize exposure of a substrate on which the array is positioned to that radiation. The wavelength λ of the reflected radiation may be selected as described above by adjusting the effective refractive index (n) and the distance (d) between the layers.

The refractive index of the matrix composition also may be adjusted to alter the difference between the refractive index of the particles and the refractive index of the matrix by adding nanoscale particles (sized 1 to 50 nm) to the matrix. The nanoscale particles have particle sizes less than the wavelength of visible light and, thus, do not substantially reflect or scatter light. Suitable materials for the nanoscale particles that increase the effective refractive index of the matrix include metals (for example, gold, silver, platinum, copper, titanium, zinc, nickel), metal oxides (for example, aluminum oxide, cerium oxide, zinc oxide, titanium dioxide), mixed metal oxides, metal bromides and semiconductors. Suitable materials for the nanoscale particles that decrease the effective refractive index of the matrix include metal oxides (for example, silica), mixed metal oxides and metal fluorides (for example, magnesium fluoride, calcium fluoride). Nanoscale air bubbles may also be produced in the polymer matrix to decrease refractive index of the matrix. Similarly, the refractive index of the particles may be adjusted by adding nanoscale particles to the particles.

In another embodiment of the present invention, a coating composition having a perceived color that exhibits goniochromaticity, that is, the perceived color varies with angle of illumination or observation, is produced. The goniochromatic coating composition includes one or more film forming materials (discussed below) and a plurality of the radiation diffracting material of the present invention functioning as colorants and, if desired, other additives described below. In functioning as colorants, the radiation diffracting material diffracts visible light.

The type and amount of film-forming material and other components included in the coating composition will depend in part upon the nature of the coating and its method of application. No particular measures have been found necessary to incorporate the colorants of the present invention into typical coating formulations. If desired, for the sake of improved dispensability, the colorants can first be incorporated into a polymeric vehicle in the form of a paste, optionally aided by the addition of surfactants conventionally used with other types of pigments.

The specific colorant to film-forming component ratio can vary widely so long as it provides the requisite color appearance at the desired film thickness and application solids and will depend upon the particular ingredients employed, the type of surface to be coated, the intended use of the surface, as well as such factors as the specific size of the colorants used. On a volume basis, the amount of colorant would usually be similar to that employed with other color effect pigments, such as coated micas or natural pearlescence (fishsilver). Although there are no critical limits, the effects may not be perceptible in most applications at colorant concentrations less than 0.2 volume percent, and it would be unusual for a coating to contain more than 50 volume percent of these special effect colorants (the percentages based on total solids content of the coating composition).

The special effect colorants of the present invention can be used in a wide variety of coating compositions, such as paints, inks, nail polish, and other cosmetics. These include waterborne and solvent-borne liquid coating compositions, powder coating compositions, powder slurry compositions and electrodeposition compositions. They can be used in clear coatings (i.e., those that produce cured films having substantial transparency) or they can be added to other pigments and/or dyes in colored coatings. Functionally, the coatings that may include the colorants of the present invention include primers, basecoats and topcoats, as well as any one or more of the coatings in a multi-coat combination. Compatibility of the colorants with a variety of polymer types has been observed, and it can be expected that any known film-forming polymer composition used for coatings could be used. Some of the more common families of polymer compositions used in coatings include polyurethanes, acrylic polymers, alkyd polymers, polyesters, siloxane-containing polymers, polysulfides, epoxy-containing polymers and polymers derived from epoxy-containing polymers and combinations thereof. These are known to be provided in coatings as lacquers, thermoplastics or thermosetting types of compositions. Thermosetting compositions will further include crosslinking agents, such as polyisocyanates, amino-formaldehyde aminoplasts, polyacids, polyanhydrides and combinations thereof. As used herein, "film-forming" means that the film-forming materials form a self-supporting continuous film on at least a horizontal surface upon removal of any solvents or carriers present in the composition or upon curing at ambient or elevated temperature. Inks refer to compositions that are suited for use in conventional printing processes.

Volatile materials that can be included as diluents in the liquid or powder slurry coating compositions include water and/or organic solvents, such as alcohols, ethers and ether alcohols, ketones, esters, aliphatic and alicyclic hydrocarbons and aromatic hydrocarbons as are commonly employed in the coating industry. Examples of solvents for coatings include aliphatic solvents, such as hexane, naphtha and mineral spirits; aromatic and/or alkylated aromatic solvents, such as toluene, xylene and SOLVESSO 100 (aromatic blend from Exxon Chemicals); alcohols, such as ethyl, methyl, n-propyl, isopropyl, n-butyl, isobutyl and amyl alcohol, and m-pryol; esters, such as ethyl acetate, n-butyl acetate, isobutyl acetate and isobutyl isobutyrate; ketones, such as acetone, methyl ethyl ketone, methyl isobutyl ketone, diisobutyl ketone, methyl n-amyl ketone, and isophorone, glycol ethers and glycol ether esters, such as ethylene glycol monobutyl ether, diethylene glycol monobutyl ether, ethylene glycol monohexyl ether, propylene glycol monomethyl ether, propylene glycol monopropyl ether, ethylene glycol monobutyl ether acetate, propylene glycol monomethyl ether acetate, and dipropylene glycol monomethyl ether acetate.

The coating compositions can further include one or more additives, such as UV absorbers and stabilizers, rheology control agents, surfactants, catalysts, film build additives, fillers, flatting agents, deformers, microgels, pH control additives and other pigments. Along with the colorants of the present invention, it may be useful in some cases to also include conventional pigments and dyes. These include micas, iron oxides, carbon black, titanium dioxide, aluminum flakes, bronze flakes, coated mica, nickel flakes, tin flakes, silver flakes, copper flakes and combinations thereof. Other organic coloring agents (i.e., dyes or organic pigments) could also be included. If it is desired to match the specific gravity of the polymeric and solvent components of the coating composition, the colorant content of the composition will have essentially no elemental metal components, and, preferably, essentially no metal oxide components as well.

Coated finishes, particularly for automobiles, are often provided by multiple layers of different coatings. An automobile coating may typically include an electrodeposited primer, a primer-surface coat, a colored basecoat and a clear topcoat. Additional coating layers may be used for appearance or performance purposes. The colorants of the present invention can be incorporated in an otherwise clear coat that is applied over a basecoat not containing the colorant but pigmented conventionally (i.e., a so-called "color-plus-clear" composite finish). Either or both of the basecoat and clear coat in this example may be waterborne as is known in the art.

In yet another alternative embodiment, the coating that includes the colorant can be a basecoat, over which is applied a clearcoat that does not contain the colorant. The components of the basecoat and those of the clearcoat can be any of those discussed above.

In yet another alternative embodiment, the coating that includes the colorant can be a clearcoat that is applied over a basecoat that also contains colorant. The components of the basecoat and those of the clearcoat can be any of those discussed above.

In yet another alternative embodiment, the coating that includes the colorant can be a clearcoat that is applied over a basecoat that does not contain colorant, and over which is applied another clearcoat that does not contain colorant. The components of the basecoat and those of the two clearcoats can be any of those discussed above.

The liquid or powder slurry coatings can be applied to the surface to be coated by any suitable coating process well-known to those skilled in the art, for example by dip coating, direct roll coating, reverse roll coating, curtain coating, spray coating, brush coating, gravure coating, flow coating, slot-die coating, ink-jet coating, electrodeposition and combinations thereof. Powder coatings are generally applied by electrostatic deposition.

The present invention also includes use of the radiation diffractive material in other types of carriers than a film-forming component. The radiation diffractive material may be included as a component dispersed in a cosmetic or impregnated into plastic.

The preparation and use of radiation diffractive material of the present invention is illustrated in the examples that follow. The following examples are merely illustrative of the invention and are not intended to be limiting. Unless otherwise indicated, all parts are by weight.

EXAMPLES

Example 1

Organic Polymer Matrix

An ultraviolet radiation curable organic composition was prepared via the following procedure. Diphenyl(2,4,6-trimethylbenzoyl)phosphine oxide/2-hydroxy-2-methyl-propiophenone (22.6 g), 50/50 blend from Aldrich Chemical Company, Inc., Milwaukee, Wis., in 615 g ethyl alcohol were added with stirring to 549 g of propoxylated (3) glyceryl triacrylate, 105.3 g of pentaerythritol tetraacrylate and 97.8 g of ethoxylated (5) pentaerythritol tetraacrylate all from Sartomer Company, Inc., Exton, Pa., to produce a curable organic matrix composition.

Example 2

Organic Core-Shell Particles

A dispersion of polystyrene-divinylbenzene core/styrene-methyl methacrylate-ethylene glycol dimethacrylate-divinylbenzene shell particles in water was prepared via the following procedure. 4.9 grams of sodium bicarbonate from Aldrich Chemical Company was mixed with 4090 g deionized water and added to a 12-liter flask equipped with a thermocouple, heating mantle, stirrer, reflux condenser and nitrogen inlet. The mixture was sparged with nitrogen for 40 minutes with stirring and then blanketed with nitrogen. Surfactant Aerosol MA80-I (46.0 g in 410 g deionized water) from Cytec Industries, Inc., was added to the mixture with stirring followed by a 48 g deionized water rinse. The mixture was heated to approximately 50° C. using a heating mantle. Styrene monomer (832.8 g), available from Aldrich Chemical Company, Inc., was added with stirring. The mixture was heated to 60° C. Sodium persulfate from Aldrich Chemical Company, Inc. (12.5 g in 144 g deionized water) was added to the mixture with stirring. The temperature of the mixture was held constant for 40 minutes. Under agitation, 205.4 g of divinylbenzene from Aldrich Chemical Company, Inc., was added to the mixture and the temperature was held at approximately 60° C. for 2.25 hours. Sodium persulfate from the Aldrich Chemical Company, Inc. (9.1 g in 86.4 g deionized water) was added to the mixture with stirring. A mixture of styrene (200 g), methyl methacrylate (478.8 g), ethylene glycol dimethacrylate (48 g)

and divinylbenzene (30.2 g) all available from Aldrich Chemical Company, Inc., was added to the reaction mixture with stirring. Surfactant Sipomer COPS-I (3-allyloxy-2-hydroxy-1-propanesulfonic acid 82.7 g) from Rhodia, Inc., Cranbury, N.J., was added to the reaction mixture with stirring. The temperature of the mixture was maintained at 60° C. for four hours. The resulting polymer dispersion was filtered through a five-micron filter bag. The polymer dispersion was then ultrafiltered using a 4-inch ultrafiltration housing with a 2.41-inch polyvinylidine fluoride membrane, both from PTI Advanced Filtration, Inc., Oxnard, Calif., and was pumped using a peristaltic pump at a flow rate of approximately 170 ml per second. Deionized water (3000 g) was added to the dispersion after 3000 g of ultrafiltrate had been removed. This exchange was repeated several times until 10023 g of ultrafiltrate was replaced with 10037 g of deionized water. Additional ultrafiltrate was then removed until the solids content of the mixture was 45 percent by weight.

Example 3

Particles on Substrate

The material prepared in Example 2 (1575 grams) was applied via a slot-die coater from Frontier industrial Technology, Inc., Towanda, Pa. to a polyethylene terephthalate substrate and dried at 180° F. for 30 seconds to a porous dry thickness of approximately 3.5 microns. The resulting deposited particles diffracted light at 541 nm when measured with a Cary 500 spectrophoto-meter from Varian, Inc. The particles were loosely deposited on the polyethylene terephthalate substrate and could easily be wiped off when touched lightly.

Examples 4-5

Backfilling of Particles

The curable organic matrix composition prepared in Example 1 (1389 grams) was applied into the interstitial spaces of the porous dried particles on the polyethylene terephthalate substrate prepared in Example 3 using a slot-die coater from Frontier Industrial Technology, Inc. After application, the samples were dried in an oven at 120° F. for a length of time listed in Table 1 and then ultraviolet radiation cured using a 100 W mercury lamp. The resulting flexible, transparent films viewed at 0 degrees or parallel to the observer had a red color. The same films, when viewed at 45 degrees or greater to the observer, were orange-green in color. The films were measured using a Cary 500 spectrophotometer from Varian, Inc and diffracted light as listed in Table 2.

TABLE 2

| Example | Drying Time | Wavelength |
|---------|-------------|------------|
| 4 | 2 minutes | 644 nm |
| 5 | 1 minute | 629 nm |

Example 6

Flake Milling

The material prepared in Example 4 was washed two times with a 50/50 mixture of deionized water and isopropyl alcohol. The material was then removed from the polyethylene terephthalate substrate using an air knife assembly from the Exair Corporation, Cincinnati, Ohio. The material was collected via vacuum into a collection bag. The loose material was then ground into powder using an ultra-centrifugal mill from Retsch GmbH & Co., Haan, Germany. The powder was then passed through a 38 micron and a 25 micron stainless steel sieve from Fisher Scientific International, Inc. The material in the 25 micron sieve was collected as a powder.

Example 7

Coating Composition Containing Colorant with Core-Shell Particles

The powder from Example 6 was added to a container containing the first component of a film-forming binder and a diluent. The container was capped and hand shaken for 1 minute. After shaking, the container was reopened and a crosslinking agent was added. The container was resealed and hand shaken for one minute. The resulting coating composition having the composition as listed in Table 3 was ready for spray application.

TABLE 3

| Component | Wt. % |
|-----------|-------|
| Film-forming binder[1] | 54.57 |
| Diluent[2] | 20.46 |
| Example 6 powder | 6.82 |
| Crosslinking agent[3] | 18.15 |
| Total | 100 |

[1]DCU2055, a clearcoat composition available from PPG Industries, Inc., Pittsburgh, PA.
[2]DT 870, a reducer available from PPG Industries, Inc.
[3]DCX61, a crosslinking agent available from PPG Industries, Inc.

A black coated steel panel (APR45583 available from ACT Laboratories, Inc., Hillsdale, Mich.) was scuff-sanded with a very fine Scotch-Brite Pad (abrasive pad available from the 3M Corp., Minneapolis, Minn.). The sanded panel was hand wiped and cleaned with a degreaser (DX330, available from PPG Industries, Inc.). The panel was then spray coated with the coating composition containing the material from Example 6.

The coated panel was flashed for 10 minutes at ambient conditions and was then baked at 140° F. for 30 minutes and was allowed to cure for 24 hours. The panel was scuff sanded with very fine Scotch-Brite pads and was cleaned with isopropanol. The panel was recoated with a protective clearcoat comprised of DCU2055 and DCX61.

The panel sat at ambient conditions for 10 minutes, was baked at 140° F. for 20 minutes, allowed to cure for 24 hours and was visually inspected. The coated panel at 0 degrees or parallel to the observer had a red color. The same coated panel, when viewed at 45 degrees or greater to the observer, was orange-green in color.

Although the present invention has been described with reference to specific details of certain embodiments thereof, it is not intended that such details should be regarded as limitations upon the scope of the invention except insofar as they are included in the accompanying claims.

As used herein, unless otherwise expressly specified, all numbers such as those expressing values, ranges, amounts or percentages may be read as if prefaced by the word "about", even if the term does not expressly appear. Any numerical range recited herein is intended to include all sub-ranges subsumed therein. Plural encompasses singular and vice versa. Also, as used herein, the term "polymer" is meant to refer to prepolymers, oligomers and both homopolymers and copolymers; the prefix "poly" refers to two or more.

What is claimed is:

1. A reflective article comprising:
   an article having a surface; and
   a composite material positioned on the surface, wherein the composite material reflects invisible radiation and comprises (i) an ordered periodic array of particles packed in direct contact with each other such that said array defines interstitial spaces between contacting particles and (ii) a polymeric matrix material received within the interstitial spaces, the particles each comprising a core surrounded by a shell of a non-film forming composition that is different from the matrix material.

2. The reflective article of claim 1 wherein the reflected invisible radiation is infrared radiation.

3. The reflective article of claim 1 wherein the reflected invisible radiation is ultraviolet radiation.

4. A method of controlling radiation reflected from a surface comprising:
   applying a composite material to a surface, where the composite material comprises:
   (i) an ordered periodic array of particles packed in direct contact with each other such that the array defines interstitial spaces between contacting particles and
   (ii) a polymeric matrix material received within the interstitial spaces, wherein the particles each comprise a core surrounded by a shell of a non-film forming composition that is different from the matrix material;
   exposing the surface bearing the composite material to radiation; and
   reflecting invisible radiation from the composite material on the surface.

5. The method of claim 4 wherein the reflected invisible radiation is infrared radiation.

6. The method of claim 4 wherein the reflected invisible radiation is ultraviolet radiation.

7. The method of claim 4 wherein the composite material is in particulate form.

8. The method of claim 7 wherein the particulate composite material is provided in a composite coating composition and said applying step comprises coating the surface with the composite coating composition containing the particulate composite material.

9. The method of claim 8 wherein the composite coating composition comprises a clear coating composition.

10. The method of claim 9 further comprising applying a colored coating composition onto the surface and applying the composite coating composition onto the colored coating composition.

11. The method of claim 4 wherein the composite material is in film form and said applying step comprises applying the film of composite material to the surface.

12. The method of claim 4 wherein the composite material is applied onto the surface by forming the array of core-shell particles onto the surface, applying a precursor of the polymeric matrix material onto the array, and curing the matrix material.

13. The method of claim 4 further comprising selecting the wavelength of radiation reflected from the surface by adjusting at least one of (i) the effective refractive index of the composite material and (ii) the distances between particles in the array.

14. The method of claim 13 wherein said adjusting step comprises forming the array of core-shell particles, applying a precursor composition of the polymeric matrix material onto the array and diffusing components of the precursor composition into the particles.

* * * * *